(12) United States Patent
Schaper, Jr.

(10) Patent No.: US 8,216,307 B2
(45) Date of Patent: Jul. 10, 2012

(54) RADIALLY SEGMENTED APODIZED DIFFRACTIVE MULTIFOCAL DESIGN FOR OCULAR IMPLANT

(75) Inventor: Dale T. Schaper, Jr., Lakeside, TX (US)

(73) Assignee: Novartis AG, Basel (CH)

( * ) Notice: Subject to any disclaimer, the term of this patent is extended or adjusted under 35 U.S.C. 154(b) by 346 days.

(21) Appl. No.: 12/614,752

(22) Filed: Nov. 9, 2009

(65) Prior Publication Data
US 2010/0161048 A1 Jun. 24, 2010

Related U.S. Application Data

(60) Provisional application No. 61/139,119, filed on Dec. 19, 2008.

(51) Int. Cl.
*A61F 2/16* (2006.01)
(52) U.S. Cl. .................. 623/6.29; 623/6.27; 623/6.3
(58) Field of Classification Search .................. None
See application file for complete search history.

(56) References Cited

U.S. PATENT DOCUMENTS

| | | | |
|---|---|---|---|
| 4,162,122 A | 7/1979 | Cohen |
| 4,210,391 A | 7/1980 | Cohen |
| 4,338,005 A | 7/1982 | Cohen |
| 4,340,283 A | 7/1982 | Cohen |
| 4,637,697 A | 1/1987 | Freeman |
| 4,641,934 A | 2/1987 | Freeman |
| 4,642,112 A | 2/1987 | Freeman |
| 4,655,565 A | 4/1987 | Freeman |
| 4,881,804 A | 11/1989 | Cohen |
| 4,881,805 A | 11/1989 | Cohen |
| 4,888,012 A | 12/1989 | Horn et al. |
| 4,995,714 A | 2/1991 | Cohen |
| 4,995,715 A | 2/1991 | Cohen |
| 5,017,000 A | 5/1991 | Cohen |
| 5,054,905 A | 10/1991 | Cohen |
| 5,056,908 A | 10/1991 | Cohen |
| 5,076,684 A | 12/1991 | Simpson et al. |
| 5,096,285 A | 3/1992 | Silberman |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,217,489 A | 6/1993 | Van Noy et al. |
| 5,257,132 A | 10/1993 | Ceglio et al. |
| 5,470,932 A | 11/1995 | Jinkerson |
| 5,528,322 A | 6/1996 | Jinkerson |

(Continued)

FOREIGN PATENT DOCUMENTS
CA 2602507 A1 9/2006
(Continued)

*Primary Examiner* — David H Willse
*Assistant Examiner* — Javier Blanco
(74) *Attorney, Agent, or Firm* — Jonathan E. Prejean (57) ABSTRACT

A radially segmented apodized diffractive multifocal IOL for ocular implant is provided. The ocular implant can comprise a radially segmented apodized diffractive multifocal intraocular lens optic and a number of haptics. The radially segmented apodized diffractive multifocal IOL may pass optical energy in both photopic and mesopic conditions. The radially segmented apodized diffractive multifocal IOL includes a number of radially segmented apodization zones, each radially segmented apodization zones having a unique focal length. The haptics mechanically couple to the apodized diffractive multifocal IOL optic in order to position and secure the apodized diffractive multifocal IOL within the eye. The radially segmented apodized diffractive multifocal IOL may include both a diffractive region and a refractive region.

3 Claims, 6 Drawing Sheets

U.S. PATENT DOCUMENTS

| | | |
|---|---|---|
| 5,543,504 A | 8/1996 | Jinkerson |
| 5,662,707 A | 9/1997 | Jinkerson |
| 5,699,142 A | 12/1997 | Lee et al. |
| 5,800,532 A | 9/1998 | Lieberman |
| 6,429,972 B1 | 8/2002 | Ota et al. |
| 6,432,246 B1 | 8/2002 | Blake |
| 6,536,899 B1 | 3/2003 | Fiala |
| 6,596,025 B2 | 7/2003 | Portney |
| 6,596,026 B1 | 7/2003 | Gross et al. |
| 6,599,317 B1 | 7/2003 | Weinschenk et al. |
| 6,638,305 B2 | 10/2003 | Laguette |
| 6,685,315 B1 | 2/2004 | De Carle |
| 6,695,881 B2 | 2/2004 | Peng et al. |
| 6,800,091 B2 | 10/2004 | Callahan et al. |
| 6,851,803 B2 | 2/2005 | Wooley et al. |
| 6,923,540 B2 | 8/2005 | Ye et al. |
| 6,951,391 B2 | 10/2005 | Morris et al. |
| 6,969,403 B2 | 11/2005 | Peng et al. |
| 7,025,456 B2 | 4/2006 | Morris et al. |
| 7,073,906 B1 | 7/2006 | Portney |
| 7,093,938 B2 | 8/2006 | Morris et al. |
| 7,156,516 B2 | 1/2007 | Morris et al. |
| 7,188,949 B2 | 3/2007 | Bandhauer et al. |
| 7,232,218 B2 | 6/2007 | Morris et al. |
| 7,322,695 B2 | 1/2008 | Wooley et al. |
| 7,350,916 B2 | 4/2008 | Hong et al. |
| 7,441,894 B2 | 10/2008 | Zhang et al. |
| 7,481,532 B2 | 1/2009 | Hong et al. |
| 7,572,007 B2 | 8/2009 | Simpson |
| 7,717,558 B2 | 5/2010 | Hong et al. |
| 2004/0156014 A1 | 8/2004 | Piers et al. |
| 2004/0252274 A1 | 12/2004 | Morris et al. |
| 2005/0209692 A1 | 9/2005 | Zhang |
| 2006/0055883 A1 | 3/2006 | Morris et al. |
| 2006/0066808 A1 | 3/2006 | Blum et al. |
| 2006/0098163 A1 | 5/2006 | Bandhauer et al. |
| 2006/0116764 A1 | 6/2006 | Simpson |
| 2006/0244904 A1 | 11/2006 | Hong et al. |
| 2007/0171362 A1 | 7/2007 | Simpson et al. |
| 2007/0182924 A1 | 8/2007 | Hong et al. |
| 2008/0030677 A1 | 2/2008 | Simpson |

FOREIGN PATENT DOCUMENTS

| | | |
|---|---|---|
| DE | 202005009124 U1 | 9/2005 |
| EP | 0742461 A2 | 11/1996 |
| EP | 0457553 B1 | 1/1999 |
| EP | 2045648 A1 | 4/2009 |
| WO | 9109336 A1 | 6/1991 |
| WO | 9744689 A1 | 11/1997 |
| WO | 9928769 A1 | 6/1999 |
| WO | 2006047698 A1 | 5/2006 |
| WO | 2006060480 A2 | 6/2006 |

RADIALLY SEGMENTED APODIZED DIFFRACTIVE MULTIFOCAL DESIGN FOR OCULAR IMPLANT

This application claims priority to U.S. Provisional Application Ser. No. 61/139,119 filed on Dec. 19, 2008.

TECHNICAL FIELD OF THE INVENTION

The present invention relates generally to ocular implants, and more particularly, to diffractive multifocal intraocular lenses (IOLs).

BACKGROUND OF THE INVENTION

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. Age and/or disease often cause the lens to become less transparent. Thus, vision deteriorates because of the diminished light which can be transmitted to the retina. This deficiency in the lens of the eye is medically known as a cataract. An accepted treatment for this condition is surgical removal of the lens and replacement of the lens function by an IOL.

The majority of ophthalmic lenses, including IOLs, currently used are of a monofocal design, (i.e., having a fixed focal length). The focal length of the implanted IOL generally is chosen to optimize vision at a single distance from the patient. Thus, most patients receiving an IOL still require glasses for clear distance and near vision.

Multifocal ophthalmic lens designs generally fall into one of two categories, refractive lenses and diffractive lenses. Diffractive lenses use nearly periodic microscopic structures on the lens to diffract light into several directions simultaneously. This is similar to a diffraction grating and the multiple diffraction orders focus the light into various images corresponding to different focal lengths of the lens. Diffractive multifocal contact lenses and IOLs are more fully discussed in U.S. Pat. Nos. 4,162,122, 4,210,391, 4,338,005, 4,340,283, 4,995,714, 4,995,715, 4,881,804, 4,881,805, 5,017,000, 5,054,905, 5,056,908, 5,120,120, 5,121,979, 5,121,980, 5,144,483, 5,117,306 (Cohen), U.S. Pat. Nos. 5,076,684, 5,116,111 (Simpson, et al.), U.S. Pat. No. 5,129,718 (Futhey, et al.) and U.S. Pat. Nos. 4,637,697, 4,641,934 and 4,655,565 (Freeman), the entire contents of which are incorporated herein by reference.

While a diffractive IOL may have a number of focal lengths, generally, IOLs with only two focal lengths (far and near) are the most common. As with any simultaneous vision multifocal lens, a defocused image (or images) is superimposed on the focused component because of the second lens power, but the defocused image is rarely observed by the user, who concentrates on the detail of interest. Under certain circumstances (for example, at night), the pupil diameter of the user can expand to 5 millimeters (mm) or more, and a discrete distant light source (e.g., automobile headlights or street lights) can appear to be surrounded by a "halo" or "rings". A significant component of the halo is caused by the light that is directed to the near image which becomes defocused at the retina. The visibility of the halo is affected by the diameter of the lens region directing light to the near image, the proportion of total energy directed to the near image, and the overall imaging aberrations of the eye.

SUMMARY OF THE INVENTION

Embodiments of the present invention provide a radially segmented apodized diffractive multifocal design for ocular implant. Embodiments of the ocular implant can comprise a radially segmented apodized diffractive multifocal intraocular lens (IOL) optic and a number of haptics. The radially segmented apodized diffractive multifocal IOL optic may pass optical energy in both photopic and mesopic conditions. The radially segmented apodized diffractive multifocal IOL optic can include a number of radially segmented apodization zones, each radially segmented apodization zone having a unique focal length. The haptics mechanically couple to the apodized diffractive multifocal IOL optic in order to position and secure the apodized diffractive multifocal IOL within the eye. The radially segmented apodized diffractive multifocal IOL may include both a diffractive region and a refractive region.

Other embodiments of the present invention provide a method to correct for visual impairment of aphakia. In one embodiment this involves removing a natural lens from an eye when the lens may be diseased or damaged through accident. Next a radially segmented apodized diffractive multifocal IOL may be inserted within the eye and secured and positioned with a number of haptics. The diffractive regions or zones of the radially segmented apodized diffractive multifocal IOL may simultaneously pass optical energy to both near and distant focal points. Each radially segmented apodization zone can have a unique focal length. The focal length differences can be adjusted to provide three (or more) distinct focal lengths (base power, plus two add powers) or to provide an add power with significantly extended depth of focus. Echelettes within each radially segmented apodization zone may have a smoothly reduced step height to shift the energy balance from the near image to the distant image and thus reduce the glare perceived when viewing a discrete, distant light source. Thus, the radially segmented apodized diffractive portion of the multifocal IOL may pass optical energy in bright optical conditions while the outer refractive region may pass optical energy to distance vision in dim optical conditions.

Yet another embodiment of the present invention provides a method to correct visual impairment. This method involves passing optical energy to the retina wherein the optical energy may be imaged. This optical energy is passed with a radially segmented apodized diffractive multifocal IOL typically located within the eye and used to replace the natural lens. The radially segmented apodized diffractive multifocal IOL may pass optical energy in both photopic and mesopic conditions using a number of radially segmented apodization zones having unique focal lengths. The focal length differences can be adjusted to provide three (or more) distinct focal lengths (base power, plus two add powers) or to provide an add power with significantly extended depth of focus.

Other advantages of the present invention will become more apparent to one skilled in the art upon reading and understanding the detailed description of the preferred embodiments described herein with reference to the following drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

A radially segmented apodized diffractive multifocal design for ocular implant is provided by embodiments of the present invention. Embodiments of the ocular implant can comprise a radially segmented apodized diffractive multifocal intraocular lens (IOL) optic and a number of haptics. The radially segmented apodized diffractive multifocal IOL optic may pass optical energy in both photopic and mesopic conditions. The radially segmented apodized diffractive multifocal IOL can comprise a number of radially segmented apodization zones, each radially segmented apodization zone having a unique focal length. The haptics mechanically couple to the apodized diffractive multifocal IOL optic in order to position and secure the apodized diffractive multifocal IOL within the eye. The radially segmented apodized diffractive multifocal IOL optic may include both a diffractive region and a refractive region.

Figure 1:
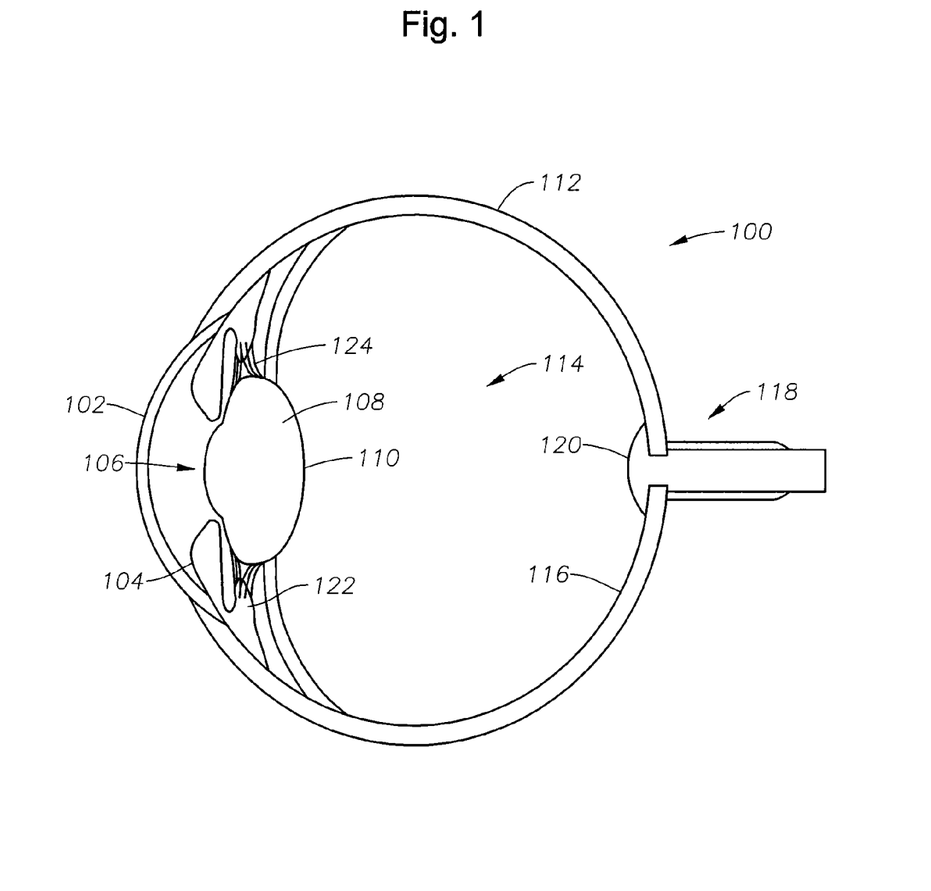
FIG. 1 illustrates the anatomy of an eye into which an embodiment of the radially segmented apodized diffractive optic design for ocular implant of the present invention may be placed.

FIG. 1 illustrates the anatomy of an eye into which embodiments of the radially segmented apodized diffractive optic design for ocular implant of the present invention may be implanted. Eye 100 includes cornea 102, iris 104, pupil 106, lens 108, lens capsule 110, zonules 124, ciliary body 122, sclera 112, vitreous gel 114, retina 116, macula 120, and optic nerve 118. Cornea 102 is a clear, dome-shaped structure on the surface of the eye through which light is admitted into eye 100. Iris 104 is the colored part of the eye and is a muscle surrounding the pupil that relaxes and contracts to control the amount of light entering the eye. Pupil 106 is the round, central opening of the iris. Lens 108 is the structure inside the eye that, together with the cornea, primarily acts to focus light on the retina 116. Lens capsule 110 is an elastic bag that envelops the lens 108, helping to control lens shape when the eye focuses on objects at different distances. Zonules 124 are slender ligaments that attach the lens capsule 110 to the inside of the eye 100, holding the lens 108 in place. The ciliary body 122 is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula 120 is the area in the back of the eye that contains functions for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonules 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

Figure 2A:
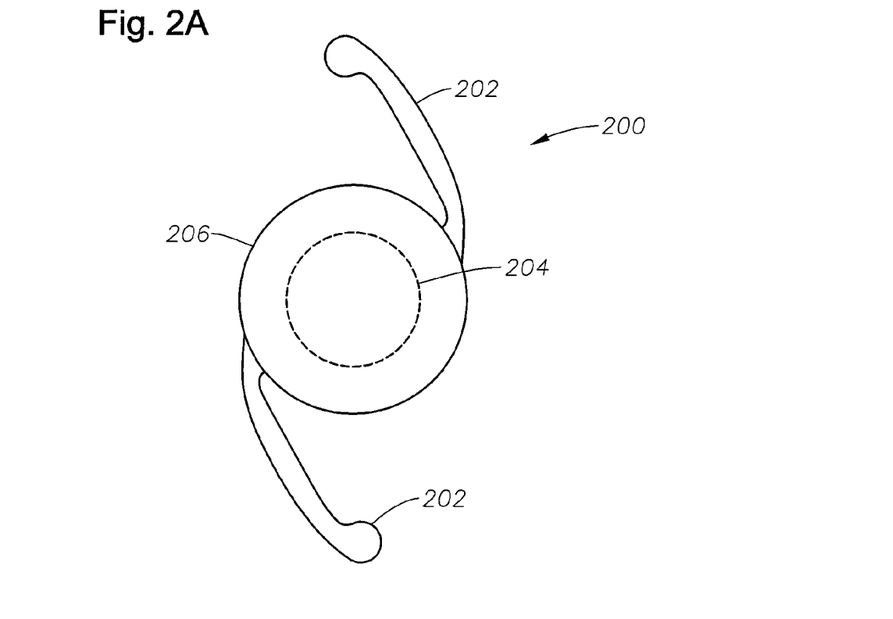
FIGS. 2A and 2B provide a top down view and a cross section of an embodiment of a radially segmented apodized diffractive IOL in accordance with the teachings of the present invention.
Figure 2B:
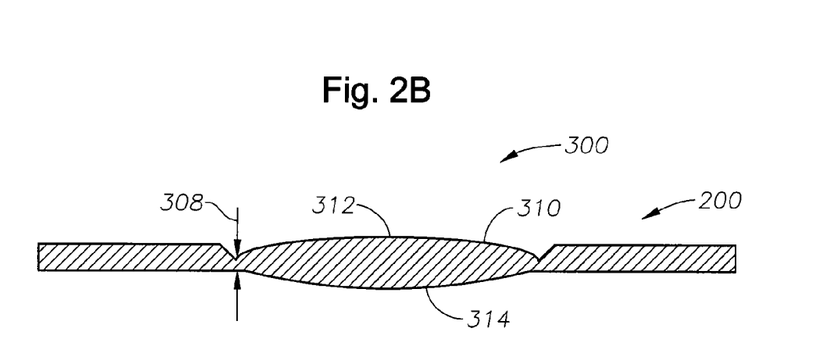

FIGS. 2A and 2B provide a top down view and a cross section of a radially segmented apodized diffractive IOL 200 in accordance with embodiments of the present invention. Radially segmented apodized diffractive IOL 200 can be an artificial lens implanted in the eye to restore vision after a natural lens has been removed. The need for the IOL 200 may be due to cataract, disease or accidents. The lens of the IOL 200 may be convex on both sides (biconvex) and may be made of a soft plastic that can be folded prior to insertion, allowing placement through an incision smaller than the optic diameter of the lens. After surgical insertion into the eye, the IOL 200 may gently unfold to restore vision. The supporting arms (haptics) 202 provide for proper positioning of the IOL 200 within the eye.

Radially segmented apodized diffractive IOL 200 may be positioned in the posterior chamber of the eye, replacing the natural lens 108. This position allows radially segmented apodized diffractive IOL 200 to correct the visual impairment of aphakia (absence of the natural lens). The radially segmented apodized diffractive pattern of IOL 200 can provide for an increased depth of focus. Radially segmented apodized diffractive IOL 200 is operable to provide near, intermediate and distance vision with increased independence from glasses in patients with and without presbyopia who have undergone cataract surgery and can provide quality vision in various lighting situations. In one embodiment, during brightly lit conditions, the central apodized diffractive portion 204 directs incoming light simultaneously to both near and distance focal points. In dimly lit conditions, the surrounding refractive area 206 sends greater energy to distance vision. The radial zones are more clearly shown in FIG. 4.

Certain embodiments of the present invention provide unique features that result in an optically stable IOL in the compressed state. These features may be implemented in various combinations and may include: (1) a reduced nominal optic edge 206 less than about 0.15 mm; and (2) angulated haptic/optic planes ensuring that any vaulting of optic 200 will occur posteriorly. The novice would expect the lens to vault in the anterior direction because of the angle of the haptics compared to the optic. The design actually creates a non-vaulting lens (when compressed to 10 mm) using a multi (double) hinged haptic design. These features result in an optically sound and stable IOL when compressed to about 10 mm or 9 mm, while maintaining acceptable force (3.0 E-04 N) in the haptics.

Haptics 202 may be molded in a single piece from the same material as optic components 204 and 206. The material used to make IOL 200 may be any soft biocompatible material capable of being folded. Suitable materials are the hydrogel, silicone or acrylic materials described in U.S. Pat. Nos. 5,411,553 (Gerace, et al.), 5,403,901 (Namdaran, et al.), 5,359,021 (Weinschenk, III, et al.), 5,236,970 (Christ, et al.), 5,141,507 (Parekh) and 4,834,750 (Gupta). Optic 310 (FIG. 2B) has an anterior side 312 and a posterior side 314 and may be of any suitable diameter, with between 4.5 mm and 7.0 mm being preferred and 5.5 mm being most preferred. Optic 310 may also be elliptical or oval. The thickness of optic 310 will vary depending on the dioptic power desired and the index of refraction for the material used, but generally will be between 0.4 mm and 1.5 mm.

Embodiments of IOL 200 may maximize the diameter of optic 310 while minimizing the size of the surgical incision. The material used to make optic 310 may be modified to absorb ultraviolet radiation, or any other desired radiation wavelength.

Figure 3:
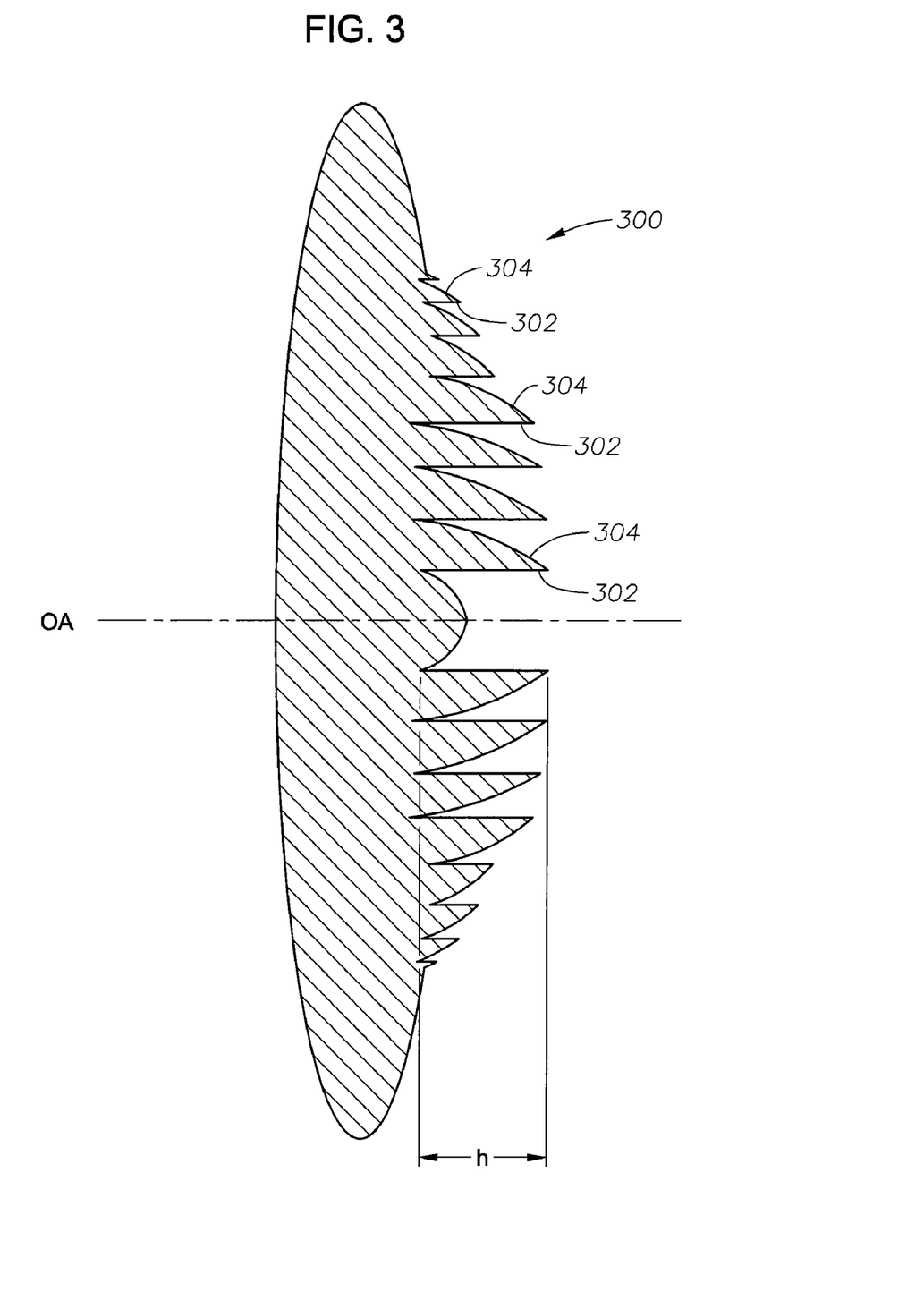
FIG. 3 provides a cross section of an embodiment of a radially segmented apodized diffractive multifocal ophthalmic lens characterized by a plurality of annular zones in accordance with the teachings of the present invention.

FIG. 3 provides a cross section 300 of an apodized diffractive multifocal ophthalmic IOL 300 characterized by a plurality of radially segmented annular zones in accordance with embodiments of the present invention. The process for determining the configuration of the radially segmented annular zones is described in U.S. Pat. No. 5,699,142 (Lee et al.), the entire contents of which are incorporated herein by reference. The boundary of each zone with respect to the optical axis is calculated. Steps 302 are placed at the radial zone boundaries between the various individual echelettes. Echelettes are diffraction grating with lines and grooves formed so as to concentrate light energy. Progressively reducing the step height (from centerline OA out to the IOL 300 edge) of a selected group of individual echelettes 304 by a predetermined amount can reduce the unwanted effects of glare perceived as a halo or rings around a distant, discrete light source. The selected group of individual echelettes to be reduced in step height is all contained in what is termed an apodization zone.

Note that the step height (h) of the echelettes 304 surrounding the optical axis (OA) remains constant over several echelettes 304 before beginning to reduce in size. Then, as the distance of each individual echelette 304 from the optical axis OA increases, the step height of each echelette 304 approaches zero. In other embodiments, the height of the echelettes 304 surrounding the optical axis OA begins diminishing with the increase in the distance of the echelette 304 from the optical axis OA. These echelettes can also be radially segmented, as shown in FIG. 4.

Figure 4:
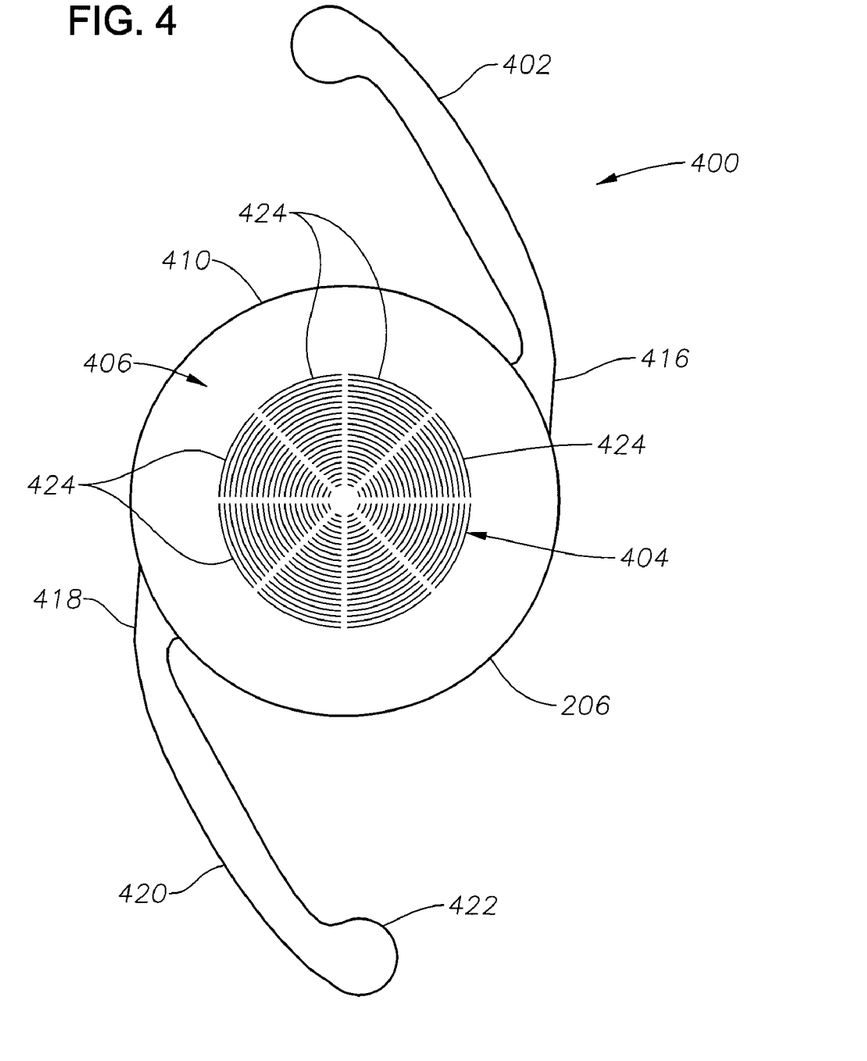
FIG. 4 provides a top down view of a radially segmented apodized diffractive multifocal ophthalmic lens characterized by a plurality of annular zones in accordance with embodiments of the present invention.

FIG. 4 provides a top down view of a radially segmented apodized diffractive multifocal ophthalmic IOL 400 characterized by a plurality of annular zones in accordance with the teachings of the present invention.

Radially segmented apodized diffractive multifocal ophthalmic lens 400 includes haptics 402, which further include gusset 416, elbow 418 and distal portion 420 having widened portion 422, optic 410, which includes central radially apodized diffractive portion 404 having radially segmented zones 424, and a surrounding refractive area 406. In one embodiment, the thickness of elbow 418 and distal portion 420 of haptic 402 is uniform, and preferably between about 0.30 mm and 0.60 mm, with between about 0.40 mm and 0.50 mm being more preferred. Gusset 416, however, has a thickness that is reduced toward anterior side 312 of the optic. Gusset 416 preferably is between about 0.15 mm and 0.60 mm thick, with between about 0.25 mm and 0.35 mm thick being more preferred. This reduced thickness generally extends from edge 206 of the optic. The relatively thin cross section of gusset 416 and edge 206 provides a thinner profile when IOL 400 is inserted through the surgical incision. The reduced thickness of gusset 416 also facilitates fluid circulation (e.g., viscoelastic) between posterior side 314 and anterior side 312. Alternatively, gusset 416 or optic 410 may be provided with other means (such as holes, grooves, notches, micro-fenestration, or protuberances (all not shown)) to facilitate fluid flow between posterior side 314 and anterior side 312 of the IOL 400/200. The relatively long length and radius of distal portion 420 provides greater contact with the capsular bag for better fixation when IOL 400 is implanted in the eye. Elbow 418 creates a hinge that allows haptic 402 to flex while minimizing buckling and vaulting of optic 410. Widened portion 422 increases the stiffness of haptic 402 just past elbow 418, thereby increasing the strength of haptic 402 at a critical stress point.

Embodiments of the present invention thus can provide a radially segmented apodized multi-focal design for an ocular implant having a profile that can help to provide improved distance vision for smaller pupils, such as under photopic conditions, and improved near vision for larger pupils compared to previously available apodized diffractive multi-focal lenses.

Some patients need clearer distance vision at smaller pupil sizes, that is, at photopic conditions. Likewise, some patients require better vision at larger pupil sizes, that is, at mesopic conditions. For example, some patients have difficulty reading menus in restaurants with dim light where the pupil could be 4 mm or larger. Embodiments of the present invention utilize the energy distribution of a multi-focal design and are optimized to achieve higher energy for distance vision at 2.75 mm or smaller pupils. At the same time, embodiments of the IOL of this invention can achieve higher energy for near vision compared to previously available ocular implants at 3.5 mm or larger pupil size.

Embodiments of this invention also provide other features for an improved ocular implant, including a thin edge for aiding in insertion through a smaller incision during the implantation surgery; an about 5 to 10% or greater improvement in MTF values at 2 and 2.5 mm or smaller pupil size as compared to previously available apodized multi-focal designs; and an about 15% or higher improvement in MTF values at 3.5 mm or larger pupil size for near vision, as compared to previously available apodized multi-focal designs. The 5 to 10% or greater improvement for smaller pupils allows for better distance vision at photopic conditions. Similarly the 15% improvement for larger pupils allows for improved near vision at mesopic or dim light conditions.

Figure 5:
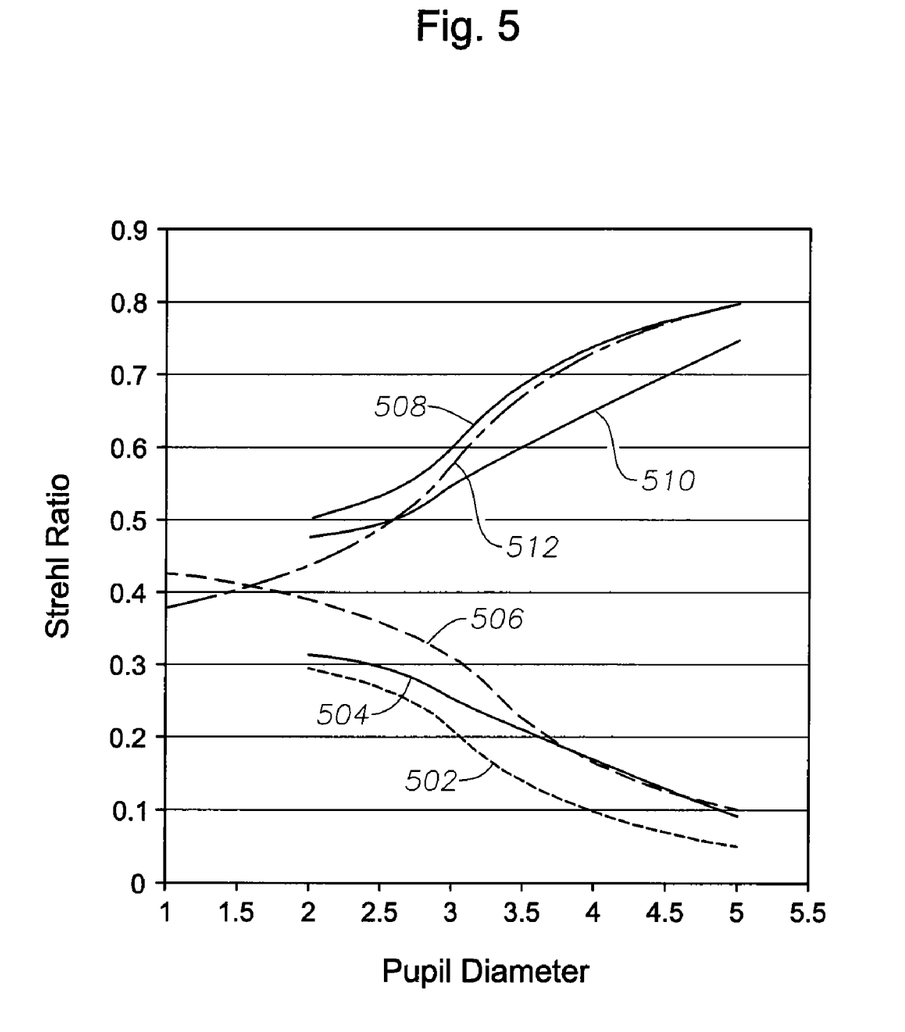
FIG. 5 is a graph depicting the Strehl Ratio for various apodized concepts and a comparison with wishbone energy distribution of previously available apodized multi-focal designs to apodized diffractive IOLs.

FIG. 5 is a graph depicting the Strehl ratio for various apodization concepts and a comparison with wishbone energy distribution of previously available apodized multi-focal designs. The Strehl ratio is an expression of optical quality. Curve 502 provides the Strehl ratio of an apodized multi-focal 3.6 mm design of an embodiment of the present invention for near vision. Curve 504 provides the Strehl ratio of an apodized multi-focal 4.5 mm design of an embodiment of the present invention for near vision. Curve 506 provides the Strehl ratio of previously available apodized multi-focal designs, such as ALCON's ReSTOR® IOL, for near conditions. Curve 508 provides the Strehl ratio of an apodized multi-focal 3.6 mm design of an embodiment of the present invention for distance vision. Curve 510 provides the Strehl ratio of an apodized multi-focal 4.5 mm design of an embodiment of the present invention for distance vision. Curve 512 provides the Strehl ratio of previously available apodized multi-focal designs, such as ALCON's ReSTOR® IOL, for distance conditions. As shown in these FIGS., embodiments of the present invention may provide clearer distance vision under photopic conditions and also better vision under mesopic conditions.

Figure 6:
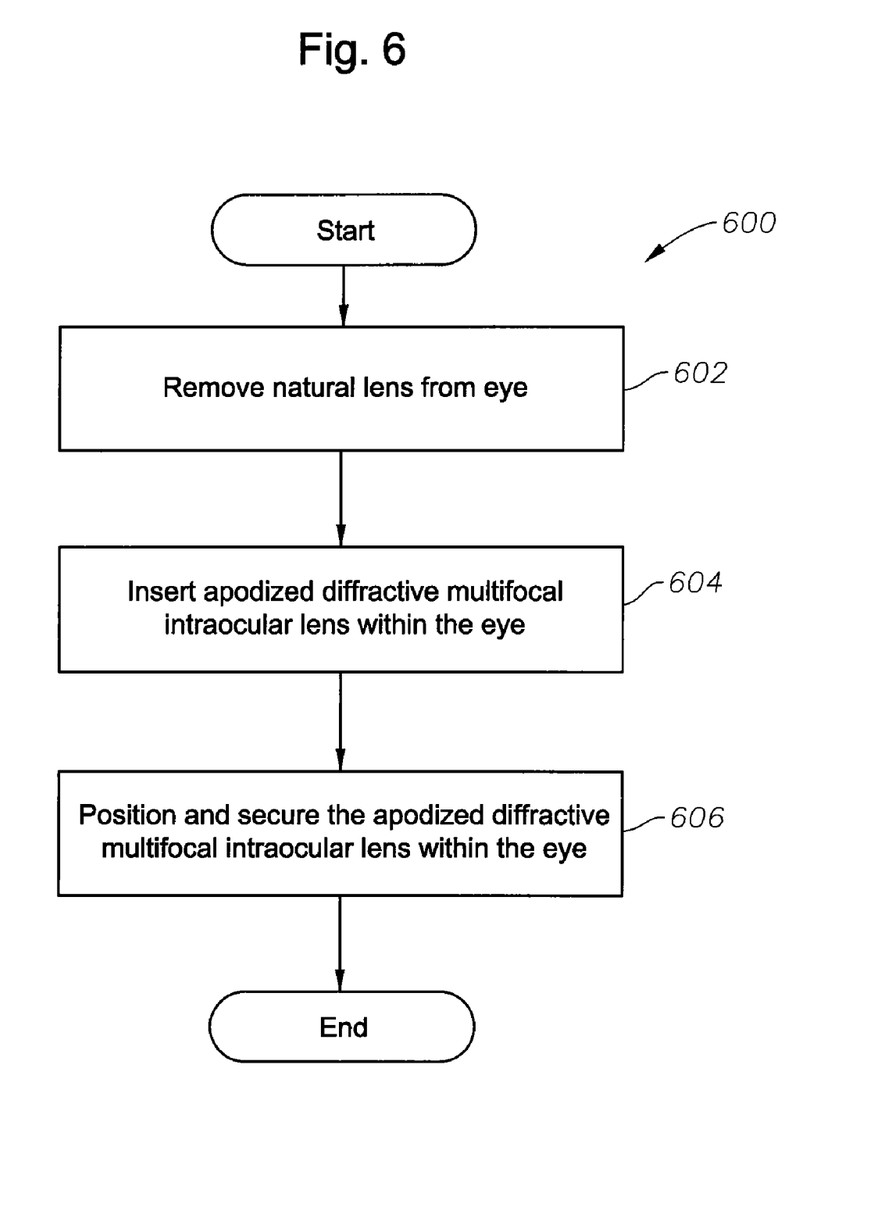
FIG. 6 is a logic flow diagram of a method to correct for visual impairments such as aphakia of the eye in accordance with embodiments of the present invention.

FIG. 6 is a logic flow diagram of a method in accordance with the teachings of this invention to correct for visual impairments such as aphakia of the eye. Procedure 600 begins with the removal of a natural lens from an eye in Step 602. An embodiment of the radially segmented apodized diffractive multi-focal IOL of the present invention may then be inserted into the eye. The lens of the radially segmented apodized diffractive multi-focal IOL may be convex on both sides (bi-convex) and made of a soft plastic that can be folded prior to insertion. This folding allows placement through a reduced-size incision wherein the incision is smaller than the optic diameter of the apodized diffractive multi-focal IOL. After surgical insertion into the eye in step 604, the IOL may gently unfold to restore vision. In Step 606, the IOL is positioned and secured within the eye. This may be done with the use of supporting arms (haptics) to provide for proper positioning of the IOL within the eye. Embodiments of the method of the present invention may place or position the IOL in the posterior chamber of the eye to replace the natural lens as shown in FIG. 1. This position allows the IOL to correct visual impairments such as the absence of a natural lens whether through disease or accident and allows patients with and without presbyopia who desire near intermediate and distant vision to experience independence from glasses following surgery such as cataract surgery.

In summary, embodiments of the present invention provide a radially segmented apodized diffractive multifocal design for ocular implant. This ocular implant (IOL) includes a radially segmented apodized diffractive multifocal optic and a number of haptics. The radially segmented apodized diffractive multifocal IOL may pass optical energy in both photopic and mesopic conditions. The radially segmented apodized diffractive multifocal IOL includes a number of radially segmented apodization zones, each radially segmented apodization zone having a unique focal length. The haptics are coupled to the apodized diffractive multifocal optic of the IOL in order to position and secure the apodized diffractive multifocal IOL within the eye.

The radially segmented apodized diffractive multifocal IOL may include both a diffractive region and a refractive region. The diffractive region may be a central region or optic zone of the lens that includes concentric steps of gradually varying step heights in order to allocate energy based on lighting conditions and activity in order to create a full range of quality vision, i.e. near to distant, for the patient.

Other embodiments of the present invention provide a method to correct for visual impairment of aphakia. In one embodiment this involves removing a natural lens from an eye when the lens may be diseased or damaged through accident. Next an apodized diffractive multifocal IOL may be inserted within the eye and then secured and positioned with a number of haptics. The diffractive region of the apodized diffractive multifocal IOL may simultaneously pass optical energy to both near and distant focal points in bright optical conditions while the outer refractive region may pass optical energy to distance vision in dim optical conditions. Yet another embodiment of the present invention provides a method to correct visual impairment. This method involves passing optical energy to the retina wherein the optical energy may be imaged. This optical energy is passed with an apodized diffractive multifocal IOL in accordance with the teachings of this invention that is typically located within the eye and used to replace the natural lens. The apodized diffractive multifocal IOL passes optical energy in both photopic and mesopic conditions. The apodized diffractive multifocal IOL can have a central diffractive region and an outer refractive region.

Embodiments of the present invention allow users to have clear distance vision at smaller pupil conditions, i.e. photopic conditions, and have improved vision at larger pupil, i.e. mesopic conditions.

As one of average skill in the art will appreciate, the term "substantially" or "approximately", as may be used herein, provides an industry-accepted tolerance to its corresponding term. As one of average skill in the art will further appreciate, the term "operably coupled", as may be used herein, includes direct coupling and indirect coupling via another component, element, circuit, or module. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship.

Although the present invention is described in detail, it should be understood that various changes, substitutions and alterations can be made hereto without departing from the spirit and scope of the invention as described by the appended claims.

What is claimed is:

1. A diffractive, multifocal intraocular lens (IOL), comprising:
   an optic, the optic comprising a central diffractive region, an outer refractive region surrounding said central diffractive region, and a thin peripheral edge for aiding in insertion through a smaller incision during implantation surgery, said central diffractive region comprising a plurality of concentric steps of gradually varying step heights, and a plurality of radially segmented apodization zones, each radially segmented apodization zone having a unique focal length and a smoothly reduced step height operable to shift an energy balance from a near image to a distant image, the optic operable to pass optical energy in both photopic and mesopic conditions;
   a plurality of haptics coupled to the optic and operable to position the diffractive multifocal IOL within an eye,
   wherein the central diffractive region is operable to pass optical energy simultaneously to both near and distant focal points in bright optical conditions; and the outer refractive region is operable to pass optical energy to distance vision in dim optical conditions.

2. The diffractive, multifocal intraocular lens of claim 1, wherein focal length differences can be adjusted to provide a plurality of distinct focal lengths.

3. The diffractive, multifocal intraocular lens of claim 1, wherein the optic comprises a biconvex optic.

\* \* \* \* \*